United States Patent [19]

Ife et al.

[11] Patent Number: 5,089,498
[45] Date of Patent: Feb. 18, 1992

[54] SUBSTITUTED 4-AMINOQUINOLINE DERIVATIVES AS GASTRIC ACID SECRETION INHIBITORS

[75] Inventors: Robert J. Ife, Aston Brook; Thomas H. Brown, Tewin; Colin A. Leach, Stevenage, all of England

[73] Assignee: SmithKline Beckman Intercredit B.V., Rotterdam, Netherlands

[21] Appl. No.: 314,624

[22] Filed: Feb. 23, 1989

[30] Foreign Application Priority Data

Feb. 25, 1988 [GB] United Kingdom ............... 8804445

[51] Int. Cl.$^5$ ............... A61K 31/47; A61K 31/535; C07D 215/14; C07D 295/182
[52] U.S. Cl. ............... 514/235.2; 514/313; 514/314; 514/212; 544/128; 546/159; 546/160; 546/161; 546/162
[58] Field of Search ............... 546/159, 160, 161, 162; 514/313, 235.2, 314, 212; 544/111, 128

[56] References Cited

U.S. PATENT DOCUMENTS

| | | | |
|---|---|---|---|
| 2,652,398 | 9/1953 | Kaye | 260/288 |
| 3,391,146 | 7/1968 | Godfrey | 546/159 |
| 3,470,186 | 9/1969 | Hanifin et al. | 260/287 |
| 4,343,804 | 8/1982 | Munson, Jr. et al. | 514/313 |
| 4,806,549 | 2/1989 | Ife et al. | 546/162 |
| 4,806,550 | 2/1989 | Ife et al. | 546/162 |

FOREIGN PATENT DOCUMENTS

| | | |
|---|---|---|
| 0245054 | 11/1987 | European Pat. Off. ............ 546/159 |
| 0258755 | 3/1988 | European Pat. Off. ............ 546/159 |
| 0259174 | 3/1988 | European Pat. Off. |
| 2106612 | 5/1972 | France |
| 2047244 | 11/1980 | United Kingdom |
| 880162 | 3/1988 | World Int. Prop. O. ............ 546/159 |

OTHER PUBLICATIONS

Robins, Chem. Abs., vol. 94, No. 21, entry #174910c (1981).

*Primary Examiner*—Mukund J. Shah
*Assistant Examiner*—E. C. Ward
*Attorney, Agent, or Firm*—Dara L. Dinner; Stephen Venetianer; Edward T. Lentz

[57] ABSTRACT

Substituted 4-aminiquinazoline derivatives of the formula:

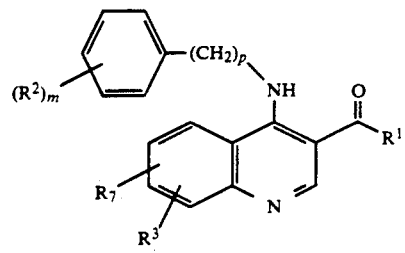

in which $R^1$ hydrogen, $C_{1-6}$ alkyl, $C_{1-6}$ alkoxy, $C_{1-6}$ alkoxy $C_{1-6}$ alkyl, $C_{3-6}$ cycloalkyl, $C_{3-6}$ cycloalkyl $C_{1-6}$ alkyl, phenyl $C_{1-6}$ alkyl, the phenyl group being optionally substituted;

$R^2$ is hydrogen, $C_{1-6}$ alkyl, $C_{1-6}$ alkoxy, amino, $C_{1-6}$ alkylthio, halogen, cyano, hydroxy, carbamoyl, carboxy, $C_{1-6}$ alkanoyl or trifluromethyl;

m is 1 to 3;

p is 0 to 4;

$R^3$ is $COR^4$;

$R^4$ is hydroxy, $C_{1-6}$ alkoxy, or $NR^5R^6$;

$R^5$ and $R^6$ are each hydrogen or $C_{1-6}$ alkyl or together with the nitrogen atom to which they are attached form a heterocyclic ring; and $R^7$ is hydrogen, $C_{1-6}$ alkoxy or $C_{1-6}$ alkyl;

or a salt thereof.

12 Claims, No Drawings

SUBSTITUTED 4-AMINOQUINOLINE DERIVATIVES AS GASTRIC ACID SECRETION INHIBITORS

The present invention relates to novel substituted quinoline derivatives, processes for their preparation, intermediates useful in their preparation, pharmaceutical compositions containing them and their use in therapy.

Substituted quinoline derivatives that inhibit gastric acid secretion are known in the art. For example, U.S. Pat. No. 4,343,804 and EP 259174-A disclose series of 4-phenylaminoquinoline compounds in which the quinoline ring is substituted by, inter alia, one or more alkyl, phenyl, alkoxy, alkylthio or halogen groups. The present invention relates to substituted quinoline derivatives comprising a novel range of substituents on the quinoline ring which have also been found to be useful in the inhibition o gastric acid secretion.

Accordingly, the present invention provides, in a first aspect, a compound of structure (I):

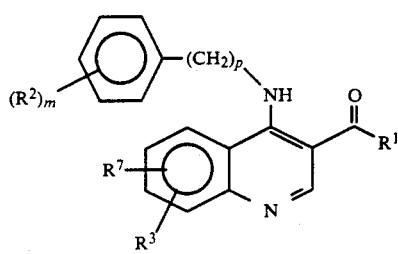

in which
$R^1$ is hydrogen, $C_{1-6}$alkyl, $C_{1-6}$alkoxy, $C_{1-6}$alkoxyC$_{1-6}$-alkyl, $C_{3-6}$cycloalkyl, $C_{3-6}$cycloalkylC$_{1-6}$alkyl, phenyl, phenylC$_{1-6}$alkyl, the phenyl groups being optionally substituted $R^2$ is hydrogen, $C_{1-6}$alkyl, $C_{1-6}$alkoxy, amino $C_{1-6}$-alkylthio, halogen, cyano, hydroxy, carbamoyl, carboxy, $C_{1-6}$alkanoyl or trifluoromethyl;

m is 1 to 3;
p is 0 to 4;
$R^3$ is $COR^4$;
$R^4$ is hydroxy, $C_{1-6}$alkoxy or $NR^5R^6$;
$R^5$ and $R^6$ are each hydrogen or $C_{1-6}$alkyl or together with the nitrogen atom to which they are attached form a heterocyclic ring; and
$R^7$ is hydrogen, hydroxy, $C_{1-6}$alkoxy or $C_{1-6}$alkyl; or a salt thereof.

Suitably, $R^1$ is hydrogen, $C_{1-6}$alkyl, $C_{1-6}$alkoxy, $C_{1-6}$alkoxyalkyl, $C_{3-6}$cycloalkyl, $C_{3-6}$cycloalkyl-C$_{1-6}$-alkyl, phenyl, or phenylC$_{1-6}$alkyl, the phenyl groups being optionally substituted. Preferably $R^1$ is hydrogen, $C_{1-6}$alkyl, $C_{1-6}$alkoxy or $C_{1-6}$alkoxyalkyl. More preferably $R^1$ is $C_{1-6}$alkyl or $C_{1-6}$alkoxy. Most preferably $R^1$ is $C_{1-6}$alkyl, in particular n-propyl.

Suitably $R^2$ is a hydrogen, $C_{1-6}$alkyl, $C_{1-6}$alkoxy, aminoC$_{1-6}$alkylthio, halogen, cyano, hydroxy, carbamoyl, carboxy, $C_{1-6}$alkanoyl, trifluoromethyl or nitro. Preferably, $R^2$ is a group other than hydrogen. More preferably $R^2$ is a substituent in the 2-position of the ring. Most preferably $R^2$ is a substituent in the 2-position of the ring, in particular a $C_{1-6}$alkyl or $C_{1-6}$alkoxy group, for example a methyl or methoxy group.

Suitably m is 1 to 3; preferably m is 1.
Suitably p is 0 to 4; preferably p is 0 to 2;
Most preferably p is 0.
Preferably $R^3$ is in the 8-position of the quinoline ring.
Suitably $R^4$ is hydroxy, $C_{1-6}$alkoxy or $NR^5R^6$, preferably $R^4$ is hydroxy or $C_{1-6}$alkoxy, for example methoxy.
Suitably $R^5$ and $R^6$ are each hydrogen or $C_{1-6}$alkyl or together with the nitrogen atom to which they are attached form a heterocyclic ring. Suitable heterocyclic ring include azetidino, pyrrolidino, piperidino and morpholino rings. Preferably $R^5$ and $R^6$ are hydrogen or $C_{1-6}$alkyl.
Suitably $R^7$ is hydrogen, $C_{1-6}$alkyl or $C_{1-6}$alkoxy, preferably $R^7$ is hydrogen or hydroxy.

$C_{1-6}$alkyl groups (either alone or as part of another group) can be straight or branched.

Phenyl $C_{1-6}$alkyl groups include for example benzyl, phenylethyl, phenylpropyl and phenylbutyl groups; and groups in which the alkyl portion is branched e.g. 1-methylbenzyl.

Substituted phenyl and phenyl $C_{1-6}$alkyl groups $R^1$ include, for example phenyl groups substituted by 1 to 3 substituents as hereinbefore described for substituted phenyl groups $R^2$.

It will be appreciated that compounds of structure (I) in which one or more of $R^1$ to $R^3$ and $R^7$ is a $C_{3-6}$alkyl group (either alone or as part of another group for example a benzyl or phenethyl group) may contain an asymmetric centre due to the presence of the $C_{3-6}$alkyl group. Such compounds will exist as optical isomers (enantiomers). Both the pure enantiomers, racemic mixture (50% of each enantiomer) and unequal mixtures of the two are included within the scope of the present invention. Further, all diastereomeric forms possible (pure enantiomers and mixtures thereof) are within the scope of the invention.

Compounds of structure (I) can form acid addition salts with suitable acids. In particular the compounds can form pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids.

In a further aspect, the present invention provides a process for the preparation of a compound of structure (I) which comprises
(a) reaction of a compound of structure (II) with a compound of structure (III):

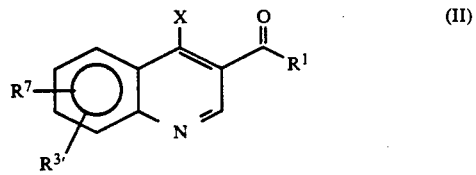

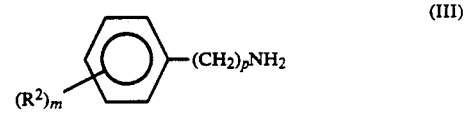

in which $R^1$, $R^2$, m, p, and $R^7$ are as described for structure (I), $R^3$, is a group $R^3$ as described for structure (I) or a protected group $R^3$ and X is a group displaceable by an amine;

(b) for compounds of structure (I) in which p is 1 to 4 reaction of a compound of structure (IV) with a compound of structure (V)

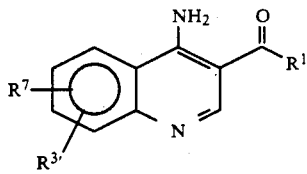

(IV)

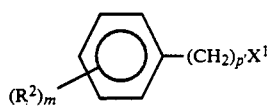

(V)

in which $R^1$, $R^2$, $R^{3'}$, m and $R^7$ are as described for structure (II); p' is 1 to 4 and $X^1$ is a leaving group;

(c) reduction of a compound of structure (VI)

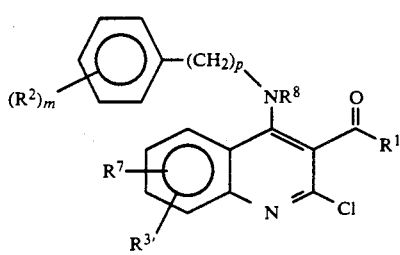

(VI)

in which $R^2$, m and p are as described for structure (I), $R^1$, $R^{3'}$ and $R^7$ are as described for structure (II); and $R^8$ is hydrogen or a nitrogen protecting group;

(d) for compounds of structure (I) in which $R^1$ is other than $C_{1-6}$alkoxy, oxidation of a compound of structure (VII)

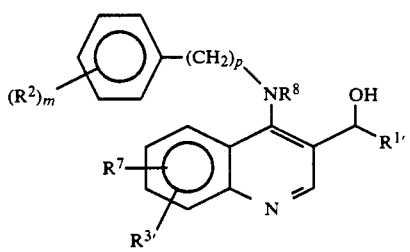

(VII)

in which $R^{1'}$ is $R^1$ as described for structure (I), but not $C_{1-6}$alkoxy, $R^2$, m and p are as described for structure (I) and $R^2$, $R^{3'}$, $R^7$ and $R^8$ are as described for structure (VI); and thereafter if desired,
removing any protecting groups;
converting a group $R^1$ into another group $R^1$;
converting one group $R^3$ into another group $R^3$;
forming a salt.

Suitable groups X displaceable by an amine, include for example, halo groups, aryl or alkylsulphonates, for example, toluene-p-sulphonate or methane sulphonate, alkylthio, alkylsulphonyl, alkylsulphinyl, alkoxy or aryloxy groups. Preferably X is a halo moiety, for example, chloro or bromo, or an aryloxy group such as phenoxy.

Suitable leaving groups $X^1$ will be apparent to those skilled in the art and include for example a halo moiety, preferably chloro or bromo.

Suitable nitrogen protecting groups $R^8$ and groups to protect the hydroxy group(s) in $R^{3'}$ will be apparent to those skilled in the art for example as described in "Protective Groups in Organic Synthesis" T.W. Greene, 1981 (Wiley) Suitable protected groups $R^3$ include for example carboxymethyl groups such as $CO_2CH_3$.

The reaction between compounds of structure (II) and compounds of structure (III) is carried out in an organic solvent at a temperature of between ambient and reflux temperature of the solvent used. Suitable solvents include, for example, tetrahydrofuran, dioxan or anisole. Preferably the reaction is carried out at reflux temperature in dioxan as a solvent.

The reaction between compounds of structure (IV) and compounds of structure (V) is carried out in an organic solvent at a temperature of between ambient and reflux temperature of the solvent used, preferably in the presence of a base. Suitable solvents include for example, dimethylsulphoxide or tetrahydrofuran. Suitable bases include for example, sodium hydride, lithium diisopropylamide and dimsyl sodium (the sodium salt of dimethylsulphoxide).

The reduction of a compound of structure (VI) is carried out by for example hydrogenation, over a noble metal catalyst in a suitable solvent. Suitably the reaction is carried out over a palladium on carbon catalyst in ethanol as a solvent.

The compounds of structure (VI) can be prepared from the corresponding compounds of structure (VIII)

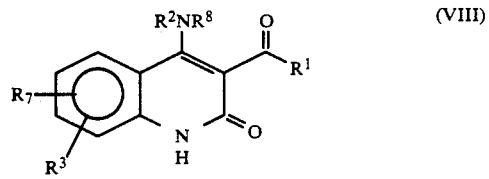

(VIII)

in which $R^1$, $R^2$, $R^3$, $R^4$ and n are as hereinbefore described, by reaction with, for example, phosphorus oxychloride.

The oxidation of a compound of structure (VII) is carried out in a suitable solvent in the presence of an oxidising agent. Suitable oxidising agents include, for example, manganese dioxide or chromium trioxide.

Suitable interconversions of groups $R^1$ will be apparent to those skilled in the art, for example compounds of structure (I) in which $R^1$ is $C_{2-6}$alkyl, $C_{3-6}$cycloalkylC$_{2-6}$alkyl or optionally substituted phenylC$_{1-6}$alkyl can be prepared by alkylation of the following compounds of structure (IA):

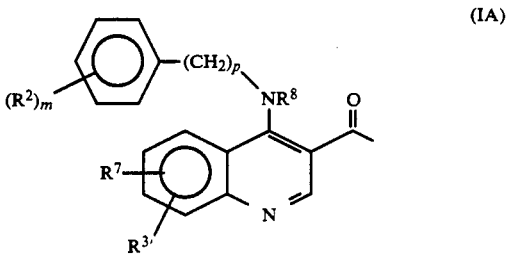

(IA)

in which $R^2$, $R^{3'}$, $R^7$, $R^8$ m and p are as described for structure (VI).

The alkylation of compounds of structure (IA) is carried out in the presence of an alkylating agent in a suitable organic solvent at a temperature of between ambient and reflux temperature of the solvent used in the presence of a strong base. Suitable alkylating agents include, for example alkyl or aralkyl halides such as methyl or benzyl iodide and dialkyl sulphates such as dimethyl or diethylsulphate. Suitable strong bases include, for example, sodium hydride, lithium diisopropylamide or dimsyl sodium (the sodium salt of dimethyl sulphoxide). Subsequent removal of any protecting groups present affords the desired compounds of structure (I).

Interconversions of the groups are possible, for example, if a compound in which $R^3$ is $CO_2Me$ is prepared, such group can be deesterified to form the corresponding compound in which $R^3$ is the free acid $CO_2H$, by reaction with, for example, a suitable alkali; or into the corresponding compound in which $R^3$ is $CONH_2$ by reaction with ammonia Further interconversions are of course possible by the application of standard chemistry.

The intermediates of structure (II), (IV), (VI), (VII) and (VIII) can be prepared by standard techniques.

The intermediates of structure (III) and (V) are commercially available or can be prepared by standard techniques.

The compounds of structure (I) and their pharmaceutically acceptable salts exert an anti-secretory effect by inhibition of the gastrointestinal $H+K+ATPase$ enzyme (Fellenius, E., Berglindh, T., Sachs, G., Olke, L., Elander, B., Sjostrand, S.E., and Wallmark, B., 1981, Nature, 290, 159–61).

In a further aspect therefore the present invention provides compounds of structure (I) and pharmaceutically acceptable salts thereof for use in therapy.

The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome. Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example piren-

EXAMPLE 1

Preparation of methyl 3-butyryl-4-(2-methylphenylamino)-quinoline-8-carboxylate

A. Preparation of ethyl 2-butyryl-3-(2-carbomethoxyphenyl-amino)acrylate

A mixture of ethyl 2-butyryl-3-ethoxyacrylate (21.4 g, 0.1 mol) and methyl anthranilate (12.9, ml, 0.1 mol) was heated to boiling for 20 minutes, then cooled and triturated with petroleum ether to obtain ethyl 2-butyryl3-(2-carbomethoxyphenylamino)acrylate as a mixture of E/Z isomers (18.0 g, 56%).

B. Preparation of methyl 3-butyryl-4(1H)-quinolone-8-carboxylate

Ethyl 2-butyryl-3-(2-carbomethoxyphenylamino)acrylate (8.63 g, 27.0 mmol) was added to boiling diphenyl ether (40 ml), and heated at reflux for 1 hour. On cooling, methyl 3-butyryl-4(1H)-quinolone-8-carboxylate (4.06 g, 55%) crystallised and was filtered off and washed with ether, m.p. 151–153°.

C. Preparation of methyl 3-butyryl-4-chloroquinoline-8-carboxylate

A solution of methyl 3-butyryl-4(1H)-quinolone-8-carboxylate (3.7 g, 13.5 mmol) in phosphoryl chloride (40 ml) was heated at reflux for 1 hour, then the phosphoryl chloride evaporated, the product poured onto ice, neutralised with sodium bicarbonate, and extracted into dichloromethane. Drying and evaporation gave methyl -butyryl-4-chloroquinoline-8-carboxylate as a brown gum (3.8 g), which was used without further purification.

D. Preparation of methyl 3-butyryl-4-(2-methylphenylamino)-quinoline-8-carboxylate A solution of methyl 3-butyryl-4-chloroquinoline-8-carboxylate (3.8 g) and 2-methylaniline (1.6 ml, 15 mmol) in 1,4-dioxan (20 ml) was heated at reflux for 30 minutes, then left to stand overnight. The solid was filtered off and washed with ethyl acetate, then converted to free base and recrystallised from methanol to obtain methyl 3-butyryl-4-(2-methylphenylamino)-quinoline-8- carboxylate (2.86 g, 56%), m.p. 113–115°.

| $C_{22}H_{22}N_2O_3$ | |
|---|---|
| Found | C 72.80, H 6.13, N 7.72 |
| Requires | C 72.91, H 6.12, N 7.73 |

EXAMPLE 2

Preparation of 3-butyryl-4-(2-methylphenylamino)quinoline-8-carboxamide

Methyl 3-butyryl-4-(2-methylphenylamino)quinoline-8-carboxylate (1.03 g, 2.8 mmol) and saturated methanol ammonia (50 ml) were heated to 140° in a pressure vessel for 4 hours. The solid which crystallised on cooling was filtered off and recrystallised from ethanol to give 3-butyryl-4-(2-methylphenylamino)quinoline-8-carboxamide (0.48 g, 49%), m.p. 185–187°.

| $C_{21}H_{21}N_3O_2 \cdot 0.25H_2O$ | |
|---|---|
| Found | C 71.82, H 6.03, N 12.06 |
| Requires | C 71.67, H 6.16, N 11.94 |

EXAMPLE 3

Preparation of 3-butyryl-4-(2-methylphenylamino)quinoline-8-carboxylic acid

Methyl 3-butyryl-4-(2-methylphenylamino)quinoline-8-carboxylate (0.3 g, 0.8 mmol) and potassium hydroxide (0.06 g, 1 mmol) were dissolved in ethanol (5 ml) and refluxed for 30 minutes, then the ethanol was evaporated, the product dissolved in water, the solution neutralised with dilute hydrochloric acid, and the solid filtered off and washed with water. Recrystallisation from ethanol gave 3-butyryl-4-(2-methyl-phenylamino)-quinoline-8-carboxylic acid (0.18 g, 62%), m.p. 179–180°.

EXAMPLE A

A tablet for oral administration is prepared by combining

| | Mg/Tablet |
|---|---|
| Compound of structure (I) | 100 |
| lactose | 153 |
| Starch | 33 |
| crospovidone | 12 |
| microcrystalline cellulose | 30 |
| magnesium stearate | 2 |
| | 330 mg | into a 9 mm tablet.

EXAMPLE B

An injection for parenteral administration is prepared from the following

| | % w:w |
|---|---|
| Compound of Example 1 | 0.50% (w:v) |
| 1M citric acid | 30% (v:v) |
| sodium hydroxide (qs) | to pH 3.2 |
| water for injection EP | to 100 ml |

The compound of Example 1 is dissolved in the citric acid and the pH slowly adjusted to pH 3.2 with the sodium hydroxide solution. The solution was then made up to 100 ml with water, sterilised by filtration and sealed into appropriately sized ampoules and vials.

Biological Data

A. $H^+K^+$ATPase Activity

The effects of a single high concentration (100 μM) of a compound of structure (I) on $K^+$-stimulated ATPase activity in lyophilised gastric vesicles was determined. Preferred compounds of structure (I) were also tested over a range of concentrations to determine $IC_{50}$ values.

(i) Preparation of lyophilised gastric vesicles (H/K-ATPase)

Lyophilised gastric vesicles were prepared from pig fundic mucosa after the method of Keeling et. al. (Biochem. Pharmacol., 34, 2967, 1985).

(ii) $K^+$-stimulated ATPase activity $K^+$-stimulated ATPase activity was determined at 37° C. in the presence of the following: 10 mM Pipes/Tris buffer pH 7.0, 2 mM $MgSO_4$, 1 mM KCl, 2 mM $Na_2ATP$ and 3-6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulph-oxide which up to the highest concentration used had no effect on $K^+$-stimulated ATPase activity.

The effect of the highest concentration of each compound of structure (I) on the recovery of a standard amount of inorganic phosphate was also determined.

(iii) Results

The compounds of Examples 1 to 3 gave $IC_{50}$ values in the rang of from 0.58 to 5.9 μM.

B. Rat Lumen Perfused Stomach (pentagastrin stimulated gastric acid secretion).

Using a modification of the procedure described by Ghosh & Schild (Br. J. Pharmacology, 13, 54, 1958), the compounds of the following examples were found on i.v. administration at a concentration of 10 μmole/kg to cause an inhibition of pentagastrin stimulated gastric acid secretion a follows:

| Example No. | % inhibition |
| --- | --- |
| 1 | 42 |
| 2 | 39 |

What is claimed is:

1. A compound of the structure (I):

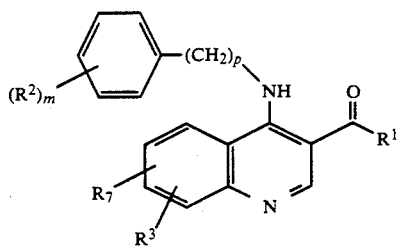

in which $R^1$ is hydrogen, $C_{1-6}$alkyl, $C_{1-6}$alkoxy, $C_{1-6}$alkoxyC$_{1-6}$alkyl, $C_{3-6}$cycloalkyl, $C_{3-6}$cycloalkylC$_{1-6}$alkyl, phenyl, or phenylC$_{1-6}$alkyl, $R^2$ is hydrogen, $C_{1-6}$alkyl, $C_{1-6}$alkoxy, amino $C_{1-6}$alkylthio, halogen, cyano, hydroxy, carbamoyl, carboxy, $C_{1-6}$alkanoyl or trifluoromethyl;

m is 1 to 3;

p is 0 to 4;

$R^3$ is $COR^4$;

$R^4$ is hydroxy, $C_{1-6}$alkoxy or $NR^5R^6$;

$R^5$ and $R^6$ are each hydrogen or $C_{1-6}$alkyl or together with the nitrogen atom to which they are attached form a heterocyclic ring selected from the group consisting of azetidino, pyrrolidino, piperidino, and morpholino; and $R^7$ is hydrogen, $C_{1-6}$alkoxy or $C_{1-6}$alkyl;

or a salt thereof.

2. The compound according to claim 1 in which $R^2$ is $C_{1-6}$alkyl, $C_{1-6}$alkoxy, amino $C_{1-6}$alkylthio, halogen, cyano, hydroxy, carbamoyl, carboxy, $C_{1-6}$alkanoyl or trifluoromethyl in the 2-position of the phenyl ring.

3. The compound according to claim 1 which is methyl 3-butyryl-4-(2methylphenylamino)quinoline-8-carboxylate.

4. The compound according to claim 1 which is 3-butyryl-4-(2-methylphenylamino)quinoline-8-carboxamide.

5. The compound according to claim 1 which is 3-butyryl-4-(2-methylphenylamino)quinoline-8-carboxylic acid.

6. The pharmaceutical composition comprising a compound according to claim 1 or a pharmaceutically acceptable salt thereof and a pharmaceutically acceptable carrier.

7. A method of inhibiting gastric acid secretion which comprises administering to a mammal in need thereof an effective amount of a compound according to claim 1.

8. A method of treatment of gastrointestinal diseases and other conditions caused or exacerbated by gastric acidity which comprises administering to a mammal in need thereof an effective amount of a compound according to claim 1.

9. The compound according to claim 2 in which $R^2$ is $C_{1-6}$alkyl.

10. The compound according to claim 1 in which p is 0.

11. The compound according to claim 1 in which $R^7$ is hydrogen.

12. The compound according to claim 9 in which $R^7$ is hydrogen, $R^2$ is methyl, and p is 0.

* * * * *